US009241977B2

(12) United States Patent
Bare et al.

(10) Patent No.: US 9,241,977 B2
(45) Date of Patent: Jan. 26, 2016

(54) ENHANCED ANABOLIC CYTOKINE PRODUCTION AND DELIVERY SYSTEM

(71) Applicant: Arthrex, Inc., Naples, FL (US)

(72) Inventors: Christopher M. Bare, Naples, FL (US); Brandon L. Roller, Naples, FL (US); Melissa S. Tucker, Bonita Springs, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 14/188,899

(22) Filed: Feb. 25, 2014

(65) Prior Publication Data

US 2014/0249071 A1 Sep. 4, 2014

Related U.S. Application Data

(60) Provisional application No. 61/771,321, filed on Mar. 1, 2013.

(51) Int. Cl.
| | | |
|---|---|---|
| *A61K 38/00* | (2006.01) | |
| *A61K 38/17* | (2006.01) | |
| *A61K 35/16* | (2015.01) | |
| *A61J 1/20* | (2006.01) | |

(52) U.S. Cl.
CPC .............. *A61K 38/1793* (2013.01); *A61K 35/16* (2013.01); *A61J 1/2089* (2013.01)

(58) Field of Classification Search
CPC .......................... A61K 35/16; A61K 38/1793
See application file for complete search history.

(56) References Cited

U.S. PATENT DOCUMENTS

| | | | | |
|---|---|---|---|---|
| 4,036,946 | A * | 7/1977 | Kleinerman | 436/531 |
| 5,059,186 | A * | 10/1991 | Yamamoto et al. | 604/537 |
| 5,766,843 | A | 6/1998 | Asgari et al. | |
| 6,713,246 | B1 | 3/2004 | Reinecke et al. | |
| 8,460,227 | B2 * | 6/2013 | Bare | C07K 14/54 604/403 |
| 8,603,345 | B2 * | 12/2013 | Ross et al. | 210/789 |
| 2004/0182784 | A1 * | 9/2004 | Walker | A61L 2/0011 210/639 |
| 2004/0186410 | A1 | 9/2004 | Davidner et al. | |
| 2004/0250587 | A1 * | 12/2004 | Zifferer | 72/96 |
| 2006/0177515 | A1 | 8/2006 | Schmieding et al. | |
| 2007/0020629 | A1 * | 1/2007 | Ross et al. | 435/6 |
| 2010/0125236 | A1 * | 5/2010 | Bare et al. | 604/6.15 |

FOREIGN PATENT DOCUMENTS

| | | |
|---|---|---|
| EP | 2 441 431 A1 | 4/2012 |
| WO | WO 96/16666 | 6/1996 |

OTHER PUBLICATIONS

Hamilton. Principles of Dialysis: Diffusion, Convection, and Dialysis Machines. Chapter 1, Kidney Atlas. 1999, pp. 1-6.*
Meijer et al. The production of anti-inflammatory cytokines in whole blood by physico-chemical induction. Inflamm. res. 52, 2003, pp. 404-407.*
Gambro, Safe and Simple. Biocomplatible and ergonomic blood tubing systems. Mar. 2010 Gambro Lundia AB, pp. 1-8.*
Goebel-Stengel et al. The importance of using the optimal plastic and glassware in studies involving peptides. Anal Biochem Jul. 2011. vol. 414, No. 1, pp. 38-46.*
W. De Jager, et al, "Improved Multiplex Immunoassay performance in human plasma and synovial fluid following removal of interfering heterophilic antibodies", Journal of Immunological Methods, Elsevier Science Publishers B.V., Amsterdam, NL, vol. 300, No. 1-2, May 1, 2005 pp. 124-135.
A. W.A. Baltzer M.D., et al. "Autologous conditioned serum (Orthokine) is an effective treatment for knee osteoarthritis", Osteoarthritis and Cartilage, Bailliere Tindall, London, GB vol. 17 No. 2 Feb. 1, 2009, pp. 152-160.
Immunoprecipitation With Dynabeads Protein A or G (Life Technologies), Rev. 8, May 2009.
L. Nokebly et al., "Immunoprecipitation With Dynabeads Protein A or G" (Invitrogen Group; wolfson.huji.ac.il/.../immunoprecipitation).
A. Holmbert et al., "The Biotin-Streptavidin Interaction Can be Reversibly Broken Using Water at Elevated Temperatures" (Electrophoresis Feb. 2005; 26 (3): 501-10; en.wikipedia.org/wiki/Streptavidin).
Ni-NTA Magnetic Agarose Beads Handbook (2nd Ed., Dec. 2001; Qiagen), pp. 12-13.

* cited by examiner

*Primary Examiner* — Marcela M Cordero Garcia
(74) *Attorney, Agent, or Firm* — Carlson, Gaskey & Olds (57) ABSTRACT

Techniques and devices for removing (filtering out) unwanted/inhibitory components (for example, products, byproducts and/or cell output such as inhibitory catabolic proteins) from a composition (for example, autologous fluid or serum) containing such unwanted/inhibitory components. The devices include at least one construct designed to contain a composition (for example, autologous fluid or serum) containing inhibitory/unwanted components (products, byproducts and/or output of cells such as inhibitory catabolic proteins). The construct is provided with interior walls including specific protein capturing means designed to remove the inhibitory/unwanted component(s) (for example, specific protein(s)) from the composition. Proteins targeted for capture include, but are not limited to, catabolic cytokines such as IL-1β, IL-α, IL-6, TNFα, IFNγ and MMPS as these proteins inhibit the healing process.

24 Claims, 7 Drawing Sheets

IL-1β Filter would reduce concentration

FIG. 7(b)

ENHANCED ANABOLIC CYTOKINE PRODUCTION AND DELIVERY SYSTEM

CROSS-REFERENCE TO RELATED APPLICATIONS

This application claims the benefit of U.S. Provisional Application No. 61/771,321, filed Mar. 1, 2013, the disclosure of which is incorporated by reference in its entirety herein.

FIELD OF THE INVENTION

The present invention relates to methods and apparatus for producing therapeutically active proteins with decreased catabolic cytokines.

BACKGROUND OF THE INVENTION

The pathogenesis of osteoarthritis involves multiple etiologies, including mechanical, biochemical, and genetic factors that contribute to the imbalance in the synthesis and destruction of articular cartilage. Pro-inflammatory cytokines such as interleukin-1beta (IL-1beta or IL-1β) and tumor necrosis factor-α are the predominant proinflammatory and catabolic cytokines involved in disease initiation and progression. Other proinflammatory cytokines may amplify or modulate this process, whereas anti-inflammatory cytokines, which are often detected in osteoarthritis tissues, may counteract the tissue destruction and inflammation.

Interleukin-1β plays a key role in the pathology of osteoarthritis or intervertebral disc generation/prolapse. The biological antagonist, interleukin-1 receptor antagonist (IL-1Ra), intervenes in the physiological mechanism of these diseases.

Systems and methods of producing serum and compositions with enhanced IL-1Ra are known in the art. For example, a system and method of producing autologeous IL-1Ra in an efficient manner are disclosed in U.S. Pat. No. 8,460,227 issued Jun. 11, 2013, the disclosure of which is incorporated by reference in its entirety herewith. The IRAP II device disclosed in U.S. Pat. No. 8,460,227 provides anti-inflammatory cytokines for treatment of human or non-human damaged tissue such as cartilage and neurological tissue, specifically IL-1Ra. Blood is withdrawn from the patient and then transferred into a special container provided with a cap configured to allow the patient's blood to flow on an inner side of the container, to ensure maximum contact with the increased surface area sides of the container. The container is then incubated and centrifuged. Subsequent to the incubation and the centrifugation, the serum containing autologeous IL-1Ra is withdrawn and injected back into the patient. Although the serum obtained with the IRAP II device has a high concentration of interleukin-1 receptor antagonist (IL-1ra), the serum also has a high concentration of interleukin 1-beta (IL-1β) and, thus, an overall low IL-1ra/IL-1β ratio.

There is a need for devices and methods for specific protein capture to promote healing responses in vivo and healing of tissue injuries. Also needed are methods and devices for selectively removing (filtering out) unwanted components (products, byproducts and/or specific output of cells) from compositions such as, e.g., autologous fluid or serum. Systems and methods of producing serum that has a high concentration of interleukin-1 receptor antagonist (IL-1ra) and reduced interleukin IL-1β (IL-1β) so that the IL-1ra inhibits the catabolic effects of IL-1β in vivo are also needed. A device that minimizes IL-1β delivered to the damaged tissue by selectively removing the cytokine and, thus, that increases the overall IL-1ra/IL-1β ratio is also needed.

SUMMARY OF THE INVENTION

The present invention provides techniques and devices for removing (filtering out) unwanted/inhibitory components (for example, products, byproducts and/or cell output such as inhibitory catabolic proteins) from a composition (for example, autologous fluid or serum) containing such unwanted/inhibitory components.

The system of the present invention comprises at least one construct designed to contain a composition (for example, autologous fluid or serum) containing inhibitory/unwanted components (products, byproducts and/or output of cells such as inhibitory catabolic proteins). The construct is provided with interior walls including specific protein capturing means designed to remove the inhibitory/unwanted component(s) (for example, specific protein(s)) from the composition. Proteins targeted for capture include, but are not limited to, catabolic cytokines such as IL-1β, IL-α, IL-6, tumor necrosis factor alpha (TNF-α), interferon gamma (IFN-γ), and matrix metalloproteinases (MMPs) as these proteins inhibit the healing process.

Other features and advantages of the present invention will become apparent from the following description of the invention, which refers to the accompanying drawings.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides techniques and devices that prevent (minimize) the introduction of catabolic cytokines into damaged tissue and/or joint space by providing specific cytokine binding before introduction (injection). The systems of the present invention provide compositions with increased anabolic and anti-inflammatory cytokines for treatment of human or non-human damaged tissue such as cartilage and neurological tissue.

The system of the present invention comprises at least one construct designed to contain (hold) a composition (for example, serum or autologous fluid such as autologous conditioned plasma (ACP), platelet rich plasma (PRP), bone marrow aspirate (BMA), and bone marrow concentrate (BMC), among others). The construct is provided with interior walls including specific protein capturing means (binding site, for example, capture antibodies with certain protein targets) designed to remove specific protein(s) from the composition. Proteins targeted for capture include, but are not limited to, IL-1β, IL-α, IL-6, TNF-α, IFN-γ, and MMPs as these proteins inhibit the healing process.

The present invention also provides methods for selectively removing (filtering out) unwanted/inhibitory components (products, byproducts and/or specific output of cells such as inhibitory catabolic proteins) from a specific composition (such as, e.g., autologous fluid or serum). The system is provided with a binding site for binding the unwanted/inhibitory component and removing such component from the composition.

In an exemplary-only embodiment, the systems and devices of the present invention bind IL-1β which plays a central role in the pathophysiology of cartilage damage and degradation in osteoarthritis. The system includes a construct (for example, a tube or vial such as a double ended tube or a capped/ribbed vial or syringe, among others) having interior walls coated with specific antibodies that are bound to the inside of the construct. When autologous fluid or serum is passed (filtered) through the construct or incubated in the construct, specific catabolic cytokines (e.g., IL-1β are bound and are selectively filtered out of the fluid (serum). In an exemplary-only embodiment, the walls are provided with specific antibodies (anti IL-1β antibodies) that remove IL-1β from serum obtained with an IRAP II system (such as the one disclosed in U.S. Pat. No. 8,460,227, the disclosure of which is incorporated in its entirety by reference herewith). In this manner, the system of the present invention minimizes IL-1β delivered to the damaged tissue by selectively binding the cytokine to the walls of the construct (tube or vial).

The present invention also provides a method of removing (filtering out) unwanted/inhibitory cell output present in an autologous fluid or serum (i.e., unwanted material produced by cells such as healing and growth inhibitory proteins) to clean the fluid (serum) and deliver the cleaned fluid (serum) to an injured site for treatment of connective tissue injuries. The method comprises the steps of (i) providing an apparatus comprising a container with walls supporting at least one protein capturing means (binding site); (ii) introducing serum (fluid) into the container; (iii) allowing the serum to interact with the protein capturing means, so that inhibitory unwanted proteins are captured by (bound to) the protein capturing means and forming a cleaned fluid (serum); and (iv) removing the cleaned serum containing less inhibitory proteins (inhibitory healing proteins) from the container.

The present invention also provides a method of providing a serum with minimized IL-1β (and increased IL-1ra/IL-1β ratio) delivered to a damaged tissue by selectively removing the IL-1β from a concentrated serum. The method comprising the steps of (i) providing a device (tube or vial) with internal walls coated with anti-IL-1β antibodies so that the anti-IL-1β antibodies are bound to the inner surface of the device; (ii) passing IRAP II serum through the device or injecting/pipetting the serum into the device; (iii) capturing the IL-1β from the serum with the coated anti-IL-1β antibodies, and removing IL-1β from the serum; and (iv) removing the cleaned serum containing less inhibitory proteins (inhibitory healing proteins), and injecting the removed serum into a patient. The system of the present invention acts as a filter to remove unwanted/inhibitory material(s) and/or byproducts produced by cells.

Referring now to the drawings, where like elements are designated by like reference numerals, FIGS. 1(a)-3(b) illustrate exemplary embodiments of device 10a, 10b, 10c of system 100 of the present invention designed to target and capture a specific protein (or multiple proteins), to promote healing responses in vivo.

Devices

The devices 10a, 10b, 10c may be have any shape/configuration and may be formed of materials such as plastics with protein binding capabilities, for example polystyrene, polyvinyl chloride (PVC), polyethylene terephalate glycol modified (PETG) or polycarbonate (PC), etc. Plastics without protein binding capabilities such as polyolefins (for example, polypropylene (PP)) are undesirable. The device/construct of the present invention may be any tube, vial, jar, syringe, tubing, etc. that can be sterilized capped, and/or closed, and that can hold any composition (for example, serum or autologous fluid such as ACP, PRP, BMA, and BMC, among many others).

Figure 1A:
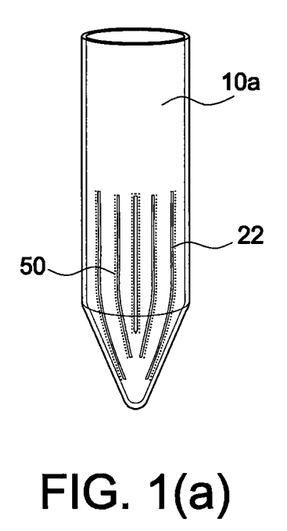
FIG. 1(a) illustrates a first exemplary embodiment of a construct (vial) coated with specific protein/antibodies of a system of the present invention (catabolic cytokines removal system).
Figure 1B:
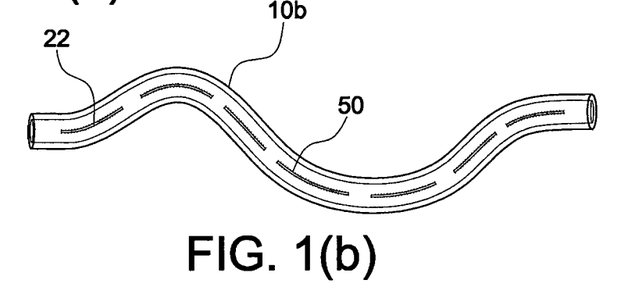
FIG. 1(b) illustrates a second exemplary embodiment of a construct (tubing) coated with specific protein/antibodies of a system of the present invention (catabolic cytokines removal system).
Figure 1C:
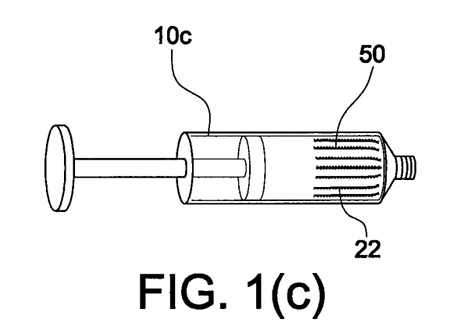
FIG. 1(c) illustrates a third exemplary embodiment of a construct (syringe) coated with specific protein/antibodies of a system of the present invention (catabolic cytokines removal system).

FIGS. 1(a)-(c) show devices 10a, 10b, 10c provided with one or more internal surfaces on the interior walls having formations that enlarge the surface area, for example, in the form of internal ribbing 22. The internal ribbing creates more surface area within the construct for more protein binding. Construct 10a may be any tube, vial, jar, etc. Construct 10b is an exemplary tube/tubing with both ends open. Construct 10c is an exemplary syringe with internal ribbing 22 provided with a protein binding site. Constructs 10a, 10b, 10c are all provided with internal walls and/or structures supporting specific protein/antibody 50 (capture antibodies 50). Each construct is coated with specific protein/antibody and serum can be incubated in the container or allowed to pass through the container (in the case of a tubing) back and forth, or just one full time.

In an exemplary embodiment, tubing construct 10b of FIG. 1(b) is provided with walls supporting specific protein/antibody 50 (capture antibodies 50). In an exemplary embodiment, tubing construct 10b is coated with the specific protein/antibody 50. Subsequent to the coating of device 10b, serum (for example, concentrated serum or fluid such as IRAP II serum) can be passed back and forth, or just once trough the tubing, from a syringe on one side of the tubing to a syringe on the other side of the tubing (as shown in FIG. 2).

Figure 2:
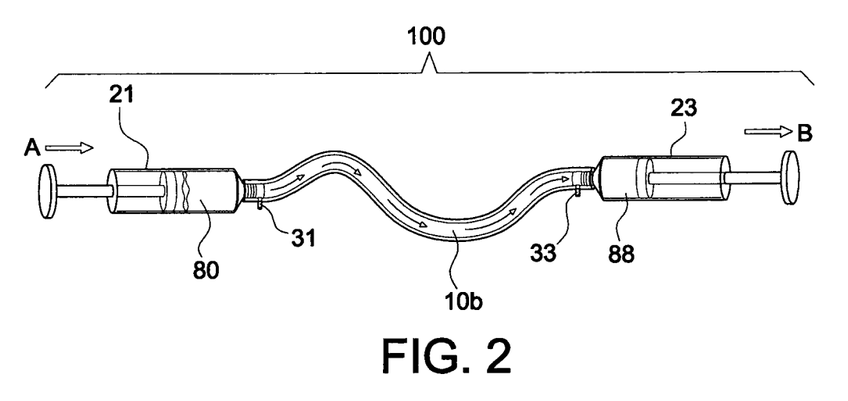
FIG. 2 illustrates the protein coated tubing of FIG. 1(b) attached to two exemplary syringes.

System 100 of FIG. 2 illustrates device 10b (protein coated tubing 10b) connected to a first syringe 21 (containing original non-treated serum 80) and to a second syringe 23 (for collecting the protein coated-tubing "treated" serum 88). Serum 80 (for example, an IRAP II serum) is pushed through the first syringe 21 in the direction of arrow A, passed through a first valve 31 into the protein coated tubing 10b and then through second valve 33 into the second syringe 22, and out of the syringe 22 in the direction of arrow B (FIG. 22). The obtained IRAP II MAX serum 88 may be further removed and injected into the body (at the specific surgical site of interest) or frozen for further injection/application.

Figure 3A:
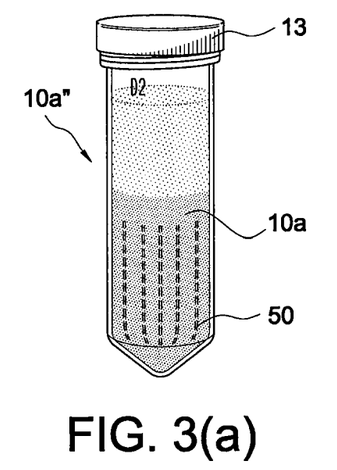
FIGS. 3(a) and 3(b) illustrate additional views of the constructs coated with specific protein/antibodies of the system of the present invention (IRAP II MAX).
Figure 3B:
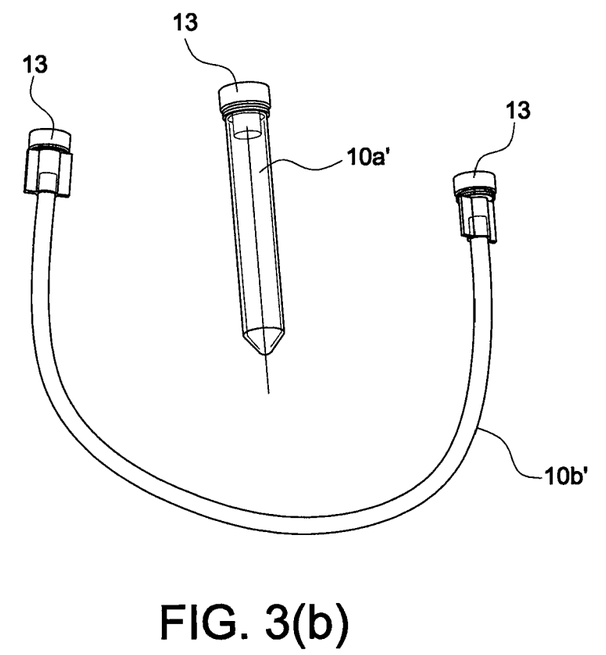

FIGS. 3(a) and 3(b) illustrate additional views of the constructs coated with specific protein/antibodies of the system of the present invention (IRAP II MAX). FIG. 3(a) shows capped vial 10a'' which includes vial 10a of FIG. 1(a) with cap 13 and serum incubated therein to allow binding of IL-1β to the specific protein site 50 formed on the inner walls of the vial 10a. FIG. 3(b) illustrates capped vial 10a' which includes vial 10a of FIG. 1(a) with cap 13 and without serum, and also tubing 10b' which include tubing 10b of FIG. 1(b) with a cap 13 at each end.

In the above-described embodiments, anti-IL-1β antibodies bound the inner surface of the device. The serum is passed through the tube. The serum is incubated in container. The IRAP II serum may be incubated in the container for a set amount of time and then it can be removed and frozen for injection. Alternatively, the IRAP II serum may be passed through the tube (tubing) and then frozen for further application/injection.

Coating of device constructs (such as devices 10a, 10b, 10c of FIGS. 1(a)-(c)) are conducted with a specific protein/antibody to capture a specific protein within serum (protein binding affinity). The specific protein/antibody is coated on at least a portion of the inner wall(s) of the devices. Proteins targeted for capture include, but are not limited to, IL-1β, IL-α, IL-6, TNFα, IFNγ and MMPS as these proteins inhibit the healing process.

Capture antibodies with certain protein targets 50 are used in a predetermined concentration to incubate within the device construct(s) 10a, 10b, 10c for a set time interval at room temperature. After the incubation period, once the capture antibodies 50 have had time to bind to the device construct(s) 10a, 10b, 10c, the device construct(s) are rinsed to remove excess proteins that have not bound. The device construct(s) 10a, 10b, 10c (coated with capture antibodies with certain protein targets 50) are then stored in a refrigerator.

Procedure

Serum 80 (such as IRAP II serum 80) is injected/pipetted into the antibody coated device construct(s) 10a, 10b, 10c. The serum is then allowed to sit in these antibody coated devices 10a, 10b, 10c in a refrigerator and for a set time period. After the serum is allowed to sit in the coated device(s) 10a, 10b, 10c, cleaned/treated serum 88 is removed and made available for injection.

Outcome

Serum 80 (FIG. 2) will interact with the capture antibodies coating the device construct(s) 10a, 10b, 10c. The unwanted proteins within the serum which cause adverse effects to the healing process will be captured or bound by the antibody coating 50 on the inside of the device construct(s) 10a, 10b, 10c. The serum 88 removed from the coated device construct(s) 10a, 10b, 10c will contain less inhibitory protein (specific to the capture antibody or antibodies) because most will be bound to the capture antibodies coating the device(s) 10a, 10b, 10c.

The devices and techniques detailed above consist of either a double ended tube 10b, or a capped/ribbed vial 10a, 10c that autologous fluid can be filtered through. What makes the tube or vial unique is the coating of specific antibodies 50 that is bound to the inside of the tube. When serum is passed through the tube or incubated in the vial, specific cytokines are bound and selectively filtered out of the fluid/serum.

In an exemplary-only embodiment, devices 10a, 10b, 10c specifically utilize the output serum 80 from the IRAP II device. However, the systems and techniques of the present invention are not limited to serum, and can be implemented with different proteins and cytokines from autologous fluids like ACP, PRP, BMA, and BMC, among others. The serum is injected into a tube or vial which has been coated with antibodies specific for IL-1β. When the serum passes through—or is injected into—the device (tube or vial or tube/vial containing an anti-body substrate), the IL-1β is taken out of solution. The ratio IL-1ra/IL-1β becomes higher and the resulting serum 88 can be injected directly into, on top, or around the damaged tissue site.

Figure 4A:
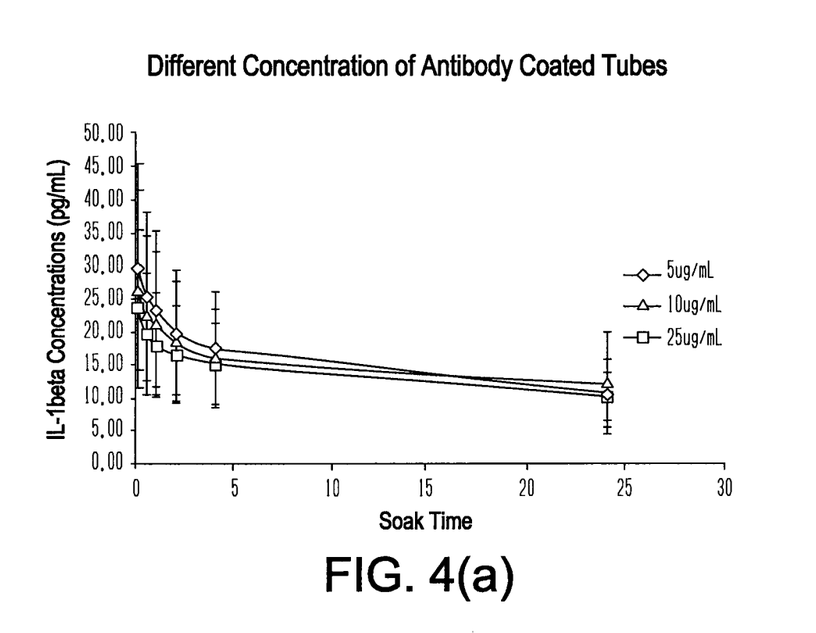
FIGS. 4(a) and 4(b) illustrate graphs with the levels of IL-1β when serum is incubated (soaked) in antibody coated devices (FIG. 4(a)) and when serum is passed through a coated device (FIG. 4(b)), and according to methods of the present invention (IRAP II MAX).
Figure 4B:
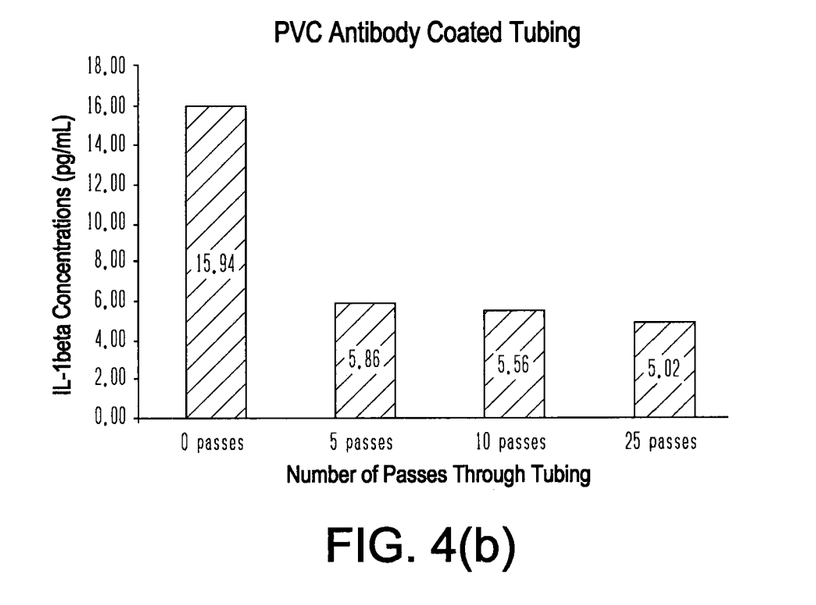

Reference is now made to FIGS. 4(a) and 4(b) which illustrate graphs with the levels of IL-1β when serum is incubated (soaked) in antibody coated devices (FIG. 4(a)) and when serum is passed through a coated device (FIG. 4(b)), and according to methods of the present invention (with the IRAP II MAX system and method). Levels of IL-1β were reduced whether incubating the serum in coated device or passing the serum through a coated tube. FIG. 4(a) shows that the IL-1β levels were reduced between 50 and 60% using the coated construct. FIG. 4(b) shows that the IL-1β levels were reduced by about 60% by passing through the coated tube.

Figure 5A:
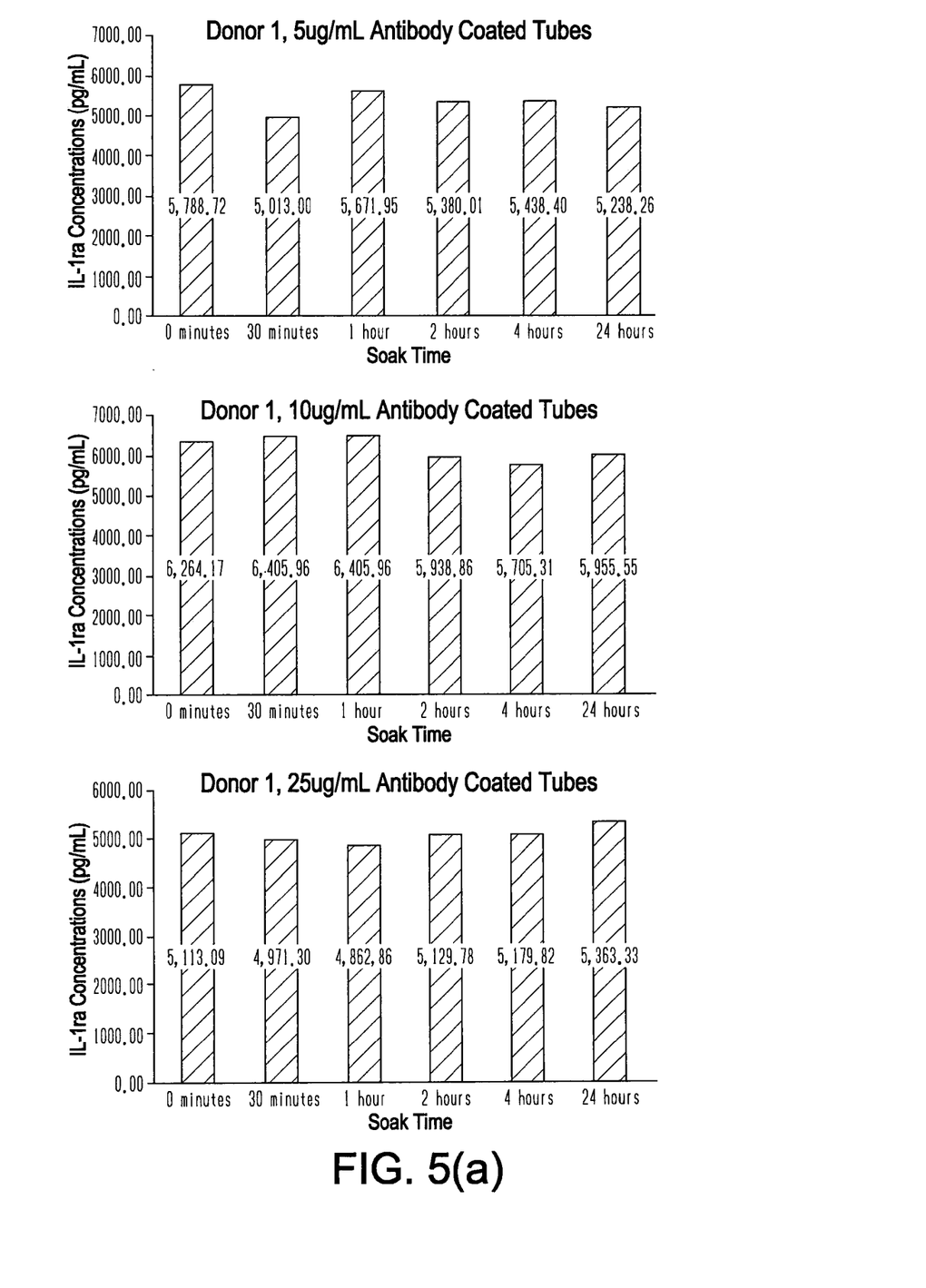
FIGS. 5(a)-(c) illustrate graphs showing that the IL-1ra levels remained about the same after passing through anti-IL-β antibodies.
Figure 5B:
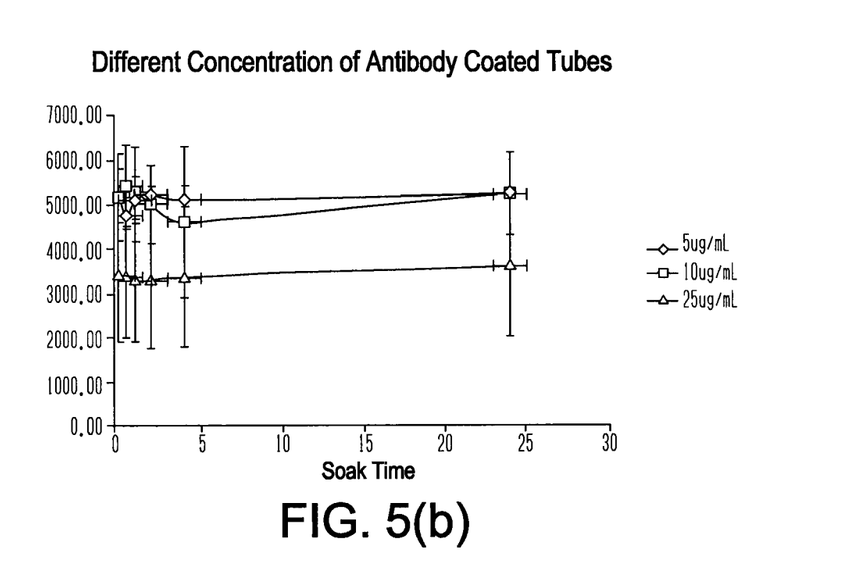
Figure 5C:
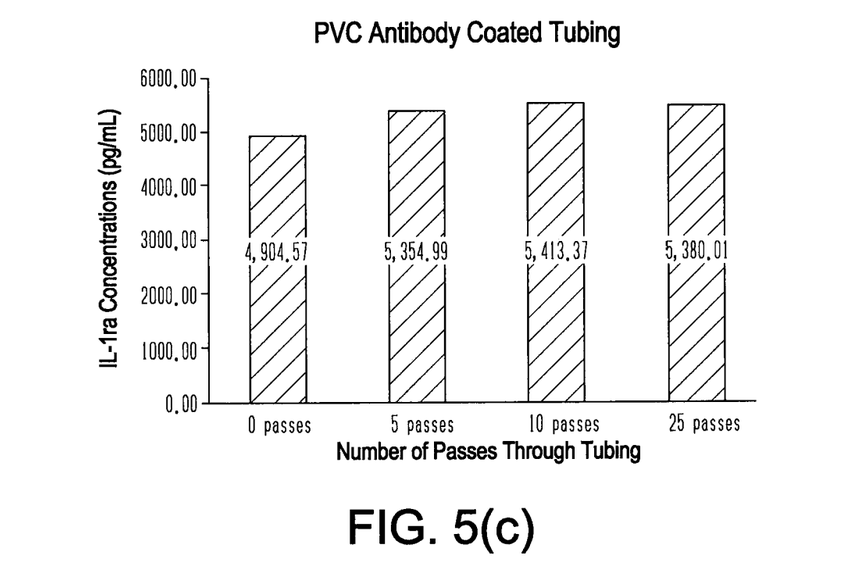

FIGS. 5(a)-(c) illustrate graphs showing that the IL-1ra levels of the IRAP II MAX system and method remained about the same after passing through anti-IL-1β antibodies. FIG. 5(a) shows the IL-1ra levels relative to various concentrations of antibody coated tubes (i.e., 5 μg/mL, 10 μg/mL and 25 μg/mL). FIG. 5(b) shows the different concentrations of the antibody coated tubes, 5 μg/mL, 10 μg/mL and 25 μg/mL. FIG. 5(c) shows that the IL-1ra levels remain about the same regardless of the number of passes through the antibody coated tubing (an exemplary PVC antibody coated tubing).

Figure 6A:
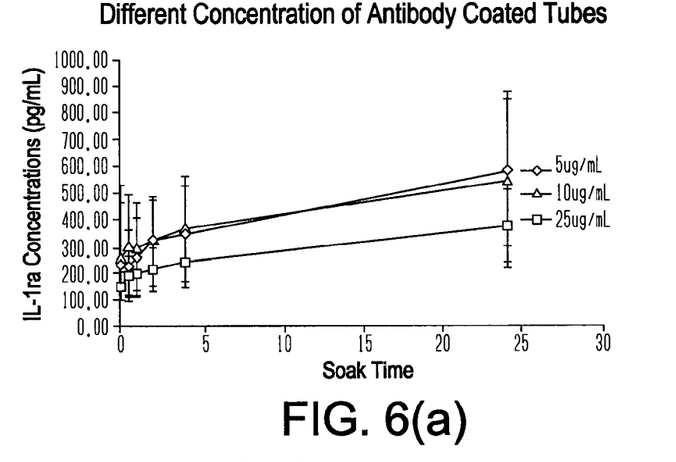
FIGS. 6(a) and 6(b) illustrate graphs with the ratio of IL-1ra/IL-1β in serum obtained with methods of the present invention (IRAP II MAX).
Figure 6B:
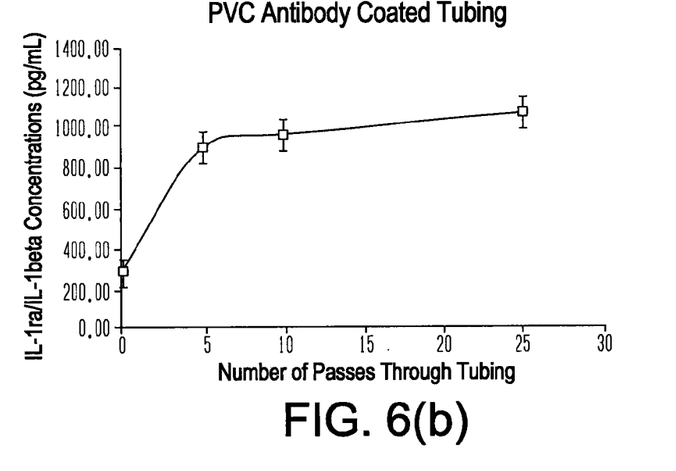
Figure 6C:
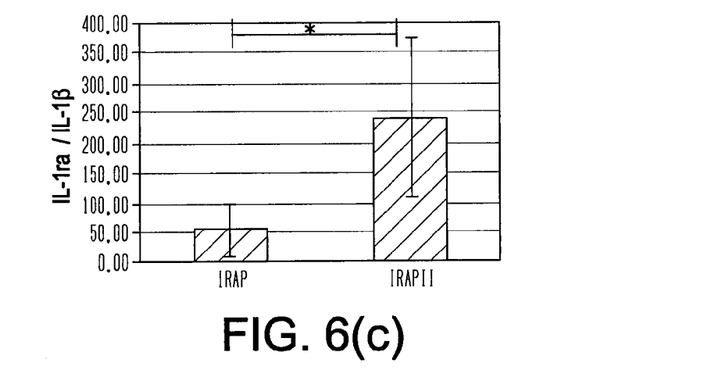
FIG. 6(c) illustrates a comparison of IRAP and IRAP II IL-1ra/IL-1β ratios.

FIGS. 6(a) and 6(b) illustrate two graphs with the ratio of IL-1ra/IL-1β in serum obtained with methods of the present invention (IRAP II MAX system and methods), i.e., by soaking/incubating in a coated device at various antibody concentrations (FIG. 6(a)) and by passing through a PVC antibody coated device between 0-25 passes (FIG. 6(b)). FIG. 6(c) illustrates a comparison of IRAP and IRAP II IL-1ra/IL-1β ratios. Due to no change in the IL-1ra concentration and the reduction in the IL-1β concentration, the IL-1ra/IL-1β ratio increases up to four times (about 4× fold).

Figure 7A:
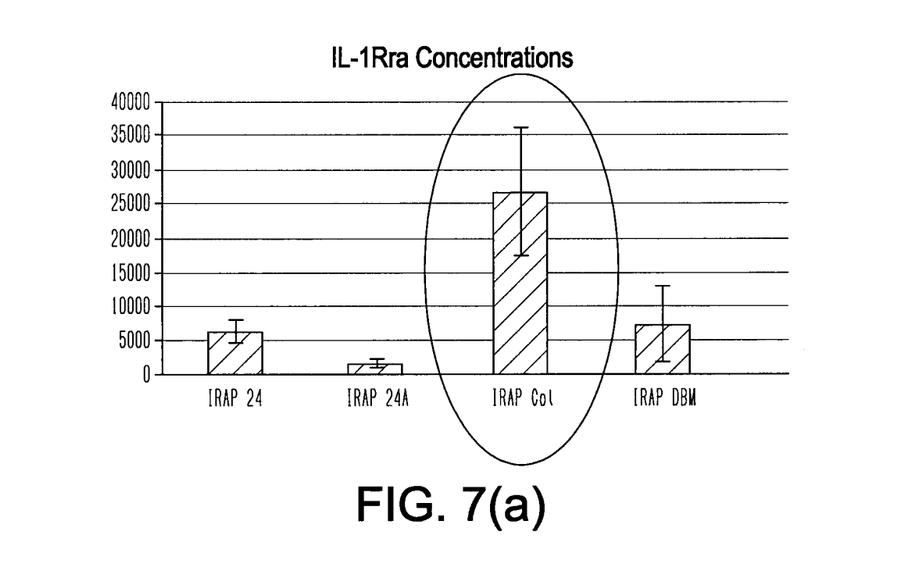
FIGS. 7(a) and 7(b) illustrate graphs with the levels of IL-1β and IL-1ra when serum is obtained with IRAP II with collagen as incubation construct.
Figure 7B:
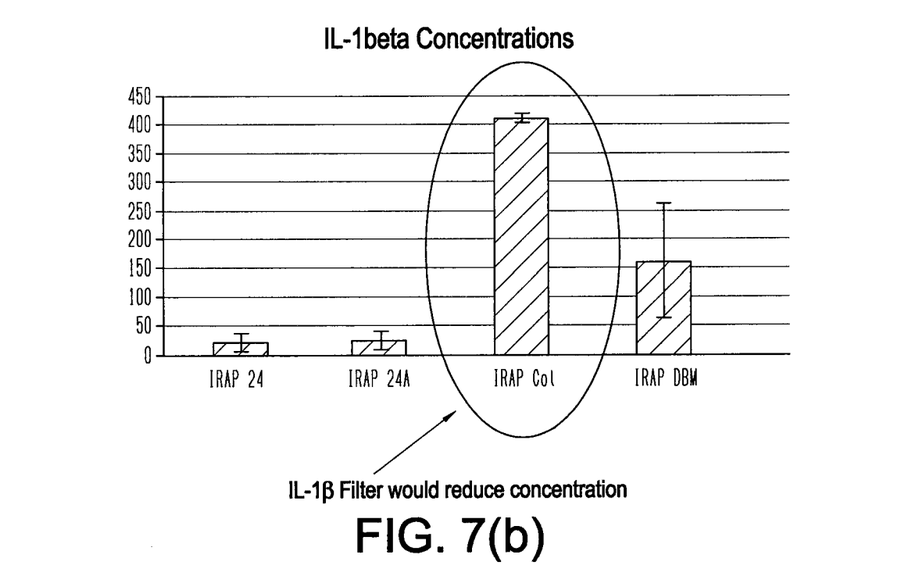

FIGS. 7(a) and 7(b) illustrate graphs with the levels of IL-1β and IL-1β when serum is obtained with IRAP II with collagen as incubation construct. FIG. 7(a) shows high IL-1ra concentrations; however, FIG. 7(b) also shows high IL-1β concentrations. Using an IRAP II MAX system of the present invention would greatly reduce the IL-1β levels while the IL-1ra elevated levels would remain still elevated. The IRAP II MAX is the IRAP II with collagen or biocartilage +IL-1β filter.

The systems and methods of the present invention (IRAP II MAX) provide the following advantages:

IL-1ra/IL-1β ratios can be maximized by selectively filtering IRAP II serum with constructs coated with anti-IL-1β (4× increase);

IRAP II MAX could be created by incubating blood with collagen or bio-cartilage, then selectively filtering with anti-IL-1β;

this technique require a minimal amount of passes through the tube to maximize IL-1β removal;

this technique allows coating of the device (tube), then packaging, labeling and sterilizing the coated device (tube), and providing the coated device in assembled (or pre-assembled) form, with overall decreased manufacturing costs; and this technique may be useful for selectively filtering out unwanted WBC with bone marrow concentrate using different anti-antibodies.

The techniques and devices of the present invention prevent/minimize the injection of catabolic cytokines into damaged tissue and/or joint space by specific cytokine binding before injection. The devices and systems of the present invention bind IL-1β which plays a central role in the pathophysiology of cartilage damage and degradation in osteoarthritis. The IRAP II device (such as the one disclosed in U.S. Pat. No. 8,460,227) produces serum that has a high concentration of interleukin 1-beta receptor antagonist (IL-1ra) and interleukin IL-1β (IL-1β). The IL-1ra inhibits the catabolic effects of IL-1β in vivo. The IRAP II MAX device and system of the present invention minimizes IL-1β delivered to the damaged tissue by selectively binding the cytokine to the walls of the tube or vial. The IRAP II MAX device of the present invention uses the output from the IRAP II device (the serum) and filters it accordingly. When serum or fluid (for example, serum from IRAP II) is passed through the tube or incubated in the vial, specific cytokines are bound and selectively filtered out of the fluid/serum.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention.

What is claimed is:

1. A method for selectively removing unwanted components from serum or autologous fluid, comprising:
   incubating the serum or autologous fluid in a construct having an internal construct wall that is coated with at least one protein binding site or passing the serum or autologous fluid through a construct having an internal construct wall that is coated with at least one protein binding site, wherein the at least one protein binding site binds a catabolic cytokine, wherein a IL-1Ra/IL-1β ratio of the serum or autologous fluid is about four times greater after the serum or autologous fluid contacts the protein binding site; and
   removing the serum or autologous fluid from the construct.

2. The method of claim 1, wherein the construct is a vial or syringe.

3. The method of claim 1, wherein the construct is tubing with two open ends.

4. The method of claim 1, wherein the internal construct wall comprises a formation that enlarges surface area.

5. The method of claim 4, wherein the formation comprises a ribbed area that is coated with the at least one protein binding site.

6. The method of claim 1, further comprising injecting the removed serum or autologous fluid into a mammal to promote tissue growth.

7. The method of claim 1, wherein the catabolic cytokine is selected from the group consisting of IL-1β, IL-α, IL-6, TNFα, IFNγ and matrix metalloproteinases.

8. The method of claim 6, wherein the injection is into damaged tissue of the mammal.

9. The method of claim 8, wherein the damaged tissue is a joint, a nerve root or a damaged tendon.

10. The method of claim 1, wherein the catabolic cytokine is IL-1β.

11. The method of claim 1, wherein the protein binding site binds IL-1β.

12. The method of claim 11, wherein the protein binding site comprises an anti-IL-1β antibody.

13. The method of claim 1, wherein the protein binding site comprises a capture antibody.

14. A method for selectively removing unwanted components from serum or autologous fluid, comprising:
   incubating the serum or autologous fluid in tubing with two open ends having internal tubing walls coated with at least one protein binding site, or passing the serum or autologous fluid through tubing having internal tubing walls coated with the at least one protein binding site, wherein the at least one protein binding site binds a catabolic cytokine, wherein an IL-1Ra/IL-1β ratio of the serum or autologous fluid is about four times greater after the serum or autologous fluid contacts the at least one protein binding site, wherein the serum or autologous fluid passes back and forth through the tubing; and
   removing the serum or autologous fluid from the tubing.

15. The method of claim 14, further comprising injecting the removed serum or autologous fluid into a mammal to promote tissue growth.

16. The method of claim 15, wherein the injection is into damaged tissue of the mammal.

17. The method of claim 16, wherein the damaged tissue is a joint, a nerve root or a damaged tendon.

18. The method of claim 14, wherein the internal tubing walls comprise a formation that enlarges surface area.

19. The method of claim 15, wherein the formation comprises a ribbed area that is coated with the at least one protein binding site.

20. The method of claim 14, wherein the catabolic cytokine is selected from the group consisting of IL-β, IL-α, IL-6, TNFα, IFNγ, and matrix metalloproteinases.

21. The method of claim 14, wherein the catabolic cytokine is IL-1β.

22. The method of claim 14, wherein the at least one protein binding site binds IL-1β.

23. The method of claim 22, wherein the at least one protein binding site comprises an anti-IL-1β antibody.

24. The method of claim 14, wherein the at least one protein binding site comprises a capture antibody.

* * * * *